(12) United States Patent
Dick et al.

(10) Patent No.: US 11,951,042 B2
(45) Date of Patent: Apr. 9, 2024

(54) DEVICE AND METHOD FOR THE PRE-DISPLAY OF A SPOT PATTERN TO BE APPLIED FOR A LASER TREATMENT OF THE EYE (71) Applicant: Carl Zeiss Meditec AG, Jena (DE)

(72) Inventors: Manfred Dick, Gefell (DE); Gerald Kunath-Fandrei, Jena (DE); René Denner, Reisdorf (DE); Thomas Wurlitzer, Leipzig (DE)

(73) Assignee: Carl Zeiss Meditec AG, Jena (DE)

( * ) Notice: Subject to any disclaimer, the term of this patent is extended or adjusted under 35 U.S.C. 154(b) by 303 days.

(21) Appl. No.: 17/045,665

(22) PCT Filed: Apr. 4, 2019

(86) PCT No.: PCT/EP2019/058444
§ 371 (c)(1),
(2) Date: Oct. 6, 2020

(87) PCT Pub. No.: WO2019/193077
PCT Pub. Date: Oct. 10, 2019

(65) Prior Publication Data
US 2021/0154048 A1 May 27, 2021

(30) Foreign Application Priority Data
Apr. 6, 2018 (DE) ...................... 10 2018 205 179.8

(51) Int. Cl.
A61F 9/008 (2006.01)

(52) U.S. Cl.
CPC ............................. A61F 9/00821 (2013.01);
A61F 2009/00863 (2013.01); A61F 2009/00897 (2013.01)

(58) Field of Classification Search
CPC ........ A61F 9/00821; A61F 2009/00863; A61F 2009/00897
See application file for complete search history.

(56) References Cited

U.S. PATENT DOCUMENTS 5,142,542 A * 8/1992 Dixon ..................... H01S 3/108
359/326
2006/0100677 A1 5/2006 Blumenkranz et al.
(Continued)

FOREIGN PATENT DOCUMENTS

DE 10 2009 021 604 A1 11/2010
EP 1 701 651 A2 9/2006
(Continued)

OTHER PUBLICATIONS

International Search Report for PCT/EP2019/058444, dated Jul. 12, 2019, 6 pages.
(Continued)

Primary Examiner — Gary Jackson
Assistant Examiner — Sebastian X Lukjan
(74) Attorney, Agent, or Firm — DeWitt LLP (57) ABSTRACT A device and method for the pre-display of a spot pattern to be applied for a laser treatment of the eye. The spot patterns to be applied are displayed to the operator in advance with the aid of a target beam. The device for the pre-display of a spot pattern to be applied for a laser treatment of the eye includes a laser system and a scanning system for generating a target beam. Here, the laser system and the scanning system for generating the target beam are formed to generate one or more lines which overlie all the spots of the spot pattern of a planned laser treatment. The device and method are suitable for laser treatment of the retina, the trabecular meshwork as well as other regions. Here, it is irrelevant whether what the laser treatment to be applied is.

18 Claims, 3 Drawing Sheets

(56) References Cited

U.S. PATENT DOCUMENTS

| | | | |
|---|---|---|---|
| 2008/0015553 A1* | 1/2008 | Zacharias | A61F 9/008 606/4 |
| 2008/0319427 A1* | 12/2008 | Palanker | A61F 9/008 606/4 |
| 2012/0150159 A1 | 6/2012 | Kunath-Fandrei et al. | |
| 2014/0228824 A1* | 8/2014 | Yee | A61F 9/00821 606/4 |

FOREIGN PATENT DOCUMENTS

| | | | | |
|---|---|---|---|---|
| EP | 2 371 328 A1 | | 10/2011 | |
| EP | 2371328 A1 | * | 10/2011 | A61F 9/00821 |
| EP | 2 391 318 A2 | | 12/2011 | |
| WO | WO-2007016749 A1 | * | 2/2007 | A61F 9/0008 |
| WO | WO-2007051061 A2 | * | 5/2007 | A61B 3/14 |
| WO | WO 2010/076799 A2 | | 7/2010 | |
| WO | WO 2014/049132 A1 | | 4/2014 | |
| WO | WO 2014/174148 A1 | | 10/2014 | |
| WO | WO-2014174148 A1 | * | 10/2014 | A61F 9/00821 |

OTHER PUBLICATIONS

English translation of International Search Report for PCT/EP2019/058444, dated Jul. 12, 2019, 3 pages.
German Search Report for 10 2018 205 179.8 dated Dec. 13, 2018, 9 pages.
Written Opinion of the ISA for PCT/EP2019/058444, dated Jul. 12, 2019, 8 pages.
English translation of the Written Opinion of the ISA for PCT/EP2019/058444, dated Jul. 12, 2019, 7 pages.
TxCell™ Scanning Laser Delivery System (product information), Iridex. Printed in U.S.A. LT0555 Dec. 2014.
(http://www.nidek-intl.com/product/ophthaloptom/laser/oph_photocoagula-tors/mc-500vixi.html), Nidek Co., Ltd., Eye and Health Care, Multi Scan Laser Photocoagulator MC-500 Vixi/MC-500, The Art of Eye Care, 2011 Japan MC-500 Vixi/MC-500, 12 pages.

* cited by examiner

DEVICE AND METHOD FOR THE PRE-DISPLAY OF A SPOT PATTERN TO BE APPLIED FOR A LASER TREATMENT OF THE EYE

TECHNICAL FIELD

Embodiments of the present invention relate to a solution for the pre-display of a spot pattern to be applied for a laser treatment of the eye. The spot patterns to be applied are to be displayed to the operator in advance with the aid of a target beam (without therapeutic effect).

BACKGROUND

According to the prior art, it is known in ophthalmology to treat the retina of the eye, or else the trabecular meshwork or other regions, by application of laser treatment. In this way, in particular, laser coagulation is used to denature tissue.

More recent, minimally invasive procedures use the thermal stimulation of the tissue with laser powers which only cause a reversible tissue change, but lead to the release of, for example, heat shock proteins such as HSP 70 and thus have a therapeutic benefit.

Furthermore, selective laser methods such as selective retina therapy or selective laser trabeculoplasty are carried out, which only selectively destroy the melanin-containing cells in the tissue, which cells are located in the retinal pigment epithelium or in the trabecular meshwork. This selective tissue destruction triggers regeneration processes in the body that likewise have a therapeutic benefit.

With all laser treatment methods, there is a desire to optimize the area coverage and, in particular, sequential multispot laser systems with scanning systems for the laser beam are used for this. Here, the systems usually have a target beam with no therapeutic effect, which gives the practitioner the opportunity to select targeted treatment areas before the actual spot patterns are applied with the aid of the therapeutic laser.

Here, different solutions have been developed in particular for the display of the spot patterns to be applied, which will be briefly discussed below.

DE 10 2009 021 604 A1 describes a method and a system for marking coagulation sites on a retina. Here, the coagulation sites are marked by projecting a serial spot sequence made of a sequential, one-dimensional sequence of individual spots. In this case, provision is furthermore made, after treatment with the coagulation laser, for carrying out a renewed serial projection of light spots as individual spots for marking a subsequent coagulation area directly adjacent to the first coagulation area.

EP 1 701 651 B1 likewise describes a solution for laser treatment of the retina at several points. Here, too, a target beam is used to display a sequence of coagulation spots on the retina. However, in contrast to the solution described above, a plurality of separate points are displayed here by application of the target beam, which points then also coincide directly with the treatment laser beam for coagulation. These points are each moved sequentially with the aid of a scanning system.

Another laser system for treating the retina is described in WO 2014/049132 A1. Again, a target beam is used to display a sequence of coagulation spots on the retina. In this solution, a pattern made of separate points is projected onto the retina, but the pattern's individual points are not all visible at once. Although both the starting point and the order of treatment are displayed to the operator, he cannot view the individual treatment locations. Here, the points marked by the target beam also coincide with the coagulation sites.

The company IRIDEX (http://www.iridex.com) offers grids for laser eye treatments, with which grids different treatment patterns with 2×2 to 7×7 laser spots can be generated (see [1]). In contrast to the solutions described above, in this case the target beam does not show the individual treatment points, but rather a visible frame surrounding the respective treatment pattern.

With the ophthalmic laser systems offered by the company NIDEK, such as, for example, the Multicolor Scan Laser Photocoagulator MC-500 Vixi (http://www.nidekintl-.com/product/ophthaloptom/laser/oph_photocoagulators/mc-500vixi.html), in the target beam mode, these systems show preferably only the corner points of the respective treatment pattern and, secondarily, all laser spot positions in a row in a changing sequence. Deviating from this, the laser coagulation takes place in rows within the displayed grid pattern.

LITERATURE

[1] TxCell™ Scanning Laser Delivery System (product information), IRIDEX. Printed in U.S.A. LT0555 December 2014

SUMMARY OF THE INVENTION

A disadvantage of the prior art solutions described here is that the operator is always presented with a sequential sequence of the potential laser spots. This results from the fact that scanning systems are used for the display. The use of slow scanning systems is disadvantageous particularly if the individual laser spots are to be displayed for a relatively long time at the location of the laser treatment spots.

Example embodiments of the present invention include the pre-display of a spot pattern to be applied for laser treatment of the eye, with which the disadvantages of the prior art are eliminated and the spot patterns can be displayed reliably and quickly. In particular, the solution allows a "stationary image" of the spot patterns to be displayed as "stationary" as possible even when using relatively slow scanning systems.

Pre-displaying a spot pattern to be applied for laser treatment of the eye is achieved in that a target beam is generated by a laser system and a scanning system, said beam being in the form of one or more lines which overlie all the spots of the spot pattern of a planned laser treatment.

According to the invention, in this case, a juxtaposed line progression is generated from the one or more lines of the target beam and is continuously displayed, as a result of which the operator is presented with an almost "stationary image" of the spot pattern.

According to a first example embodiment, the one or more line(s) of the target beam can be formed as rectilinear, curved or otherwise.

According to a further example embodiment, it is provided that the individual laser spots are additionally shown within the juxtaposed line progression. According to a further example embodiment of the invention, for this purpose, at the positions of the individual laser spots, the scan movement is decreased or briefly stopped, the intensity of the target beam is briefly increased significantly, or the wavelength of the target beam is changed significantly.

Example embodiments of the invention are intended for laser treatment of the eye, in which a spot pattern to be applied is pre-displayed by a target beam before the actual laser treatment on the eye is carried out.

The proposed solution is suitable for the laser treatment of the retina, the trabecular meshwork or else other regions.

Here, it is irrelevant whether the laser treatment is a minimally invasive method for thermal stimulation, selective retina therapy or selective laser trabeculoplasty or laser coagulation for denaturing tissue.

BRIEF DESCRIPTION OF THE DRAWINGS

The invention is described in more detail below on the basis of exemplary embodiments. In the figures.

DETAILED DESCRIPTION

According to example embodiments, a device for the pre-display of a spot pattern to be applied for a laser treatment of the eye includes a laser system and a scanning system that to gather generate a target beam. Here, the laser system and the scanning system for generating the target beam are formed to generate one or more lines which overlie all the spots of the spot pattern of a planned laser treatment.

According to example embodiments of the invention, the laser system and the scanning system are further designed to depict the one or more lines of the target beam as a juxtaposed line progression.

Regardless of how the one or more lines of the target beam are juxtaposed to make a line progression, individual or even all laser spots are arranged at the turning points, i.e. at the points with a change of direction.

When juxtaposing the one or more lines of the target beam, it is advantageous to take into account the movement of the scanning system. Spiral, meandering or zigzag juxtapositions are therefore, for example, preferable.

The juxtaposition of the one or more lines of the target beam to make a line progression is achieved by the scanning system first accelerating the target beam from a beginning of the line to the end of the line and then decelerating the target beam, in order to accelerate the next line progression at the point of direction change and then to decelerate it again until all lines are connected to form a line progression and the entire spot pattern of a planned laser treatment was displayed.

Figure 1A:
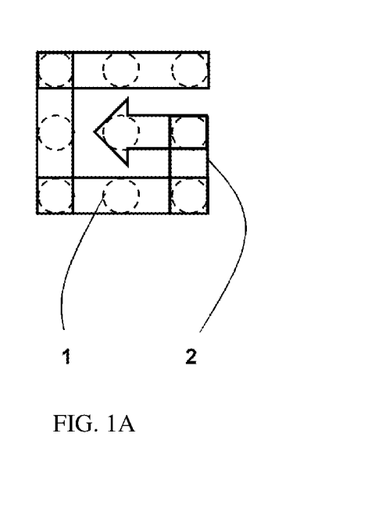
FIGS. 1A and 1B depict spiral juxtaposed line progressions of the target beam for the pre-display of a 3×3 and a 4×4 spot pattern.
Figure 1B:
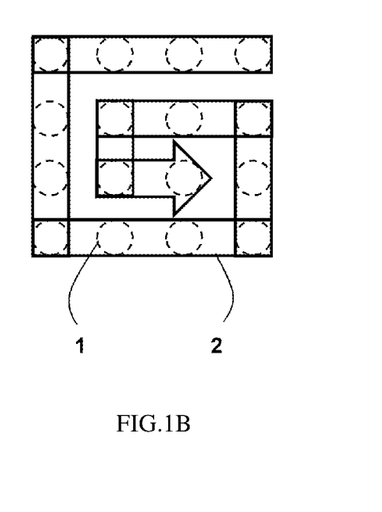
Figure 2A:
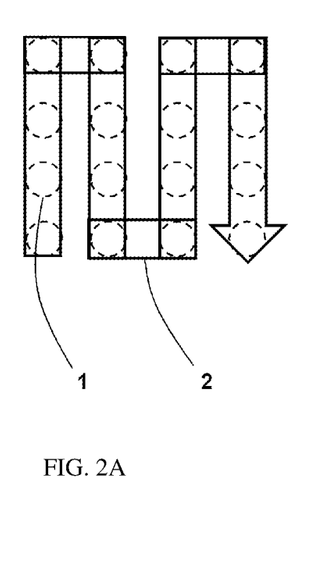
FIGS. 2A and 2B depict meandering juxtaposed line progressions of the target beam for the pre-display of a 4×4 spot pattern.
Figure 2B:
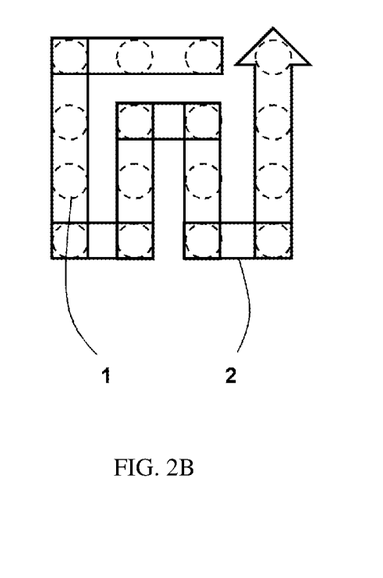
Figure 3A:
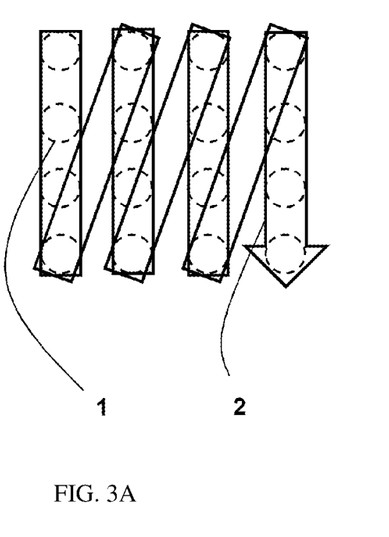
FIGS. 3A and 3B depict two zigzag juxtaposed line progressions of the target beam for the pre-display of a 4×4 spot pattern.
Figure 3B:
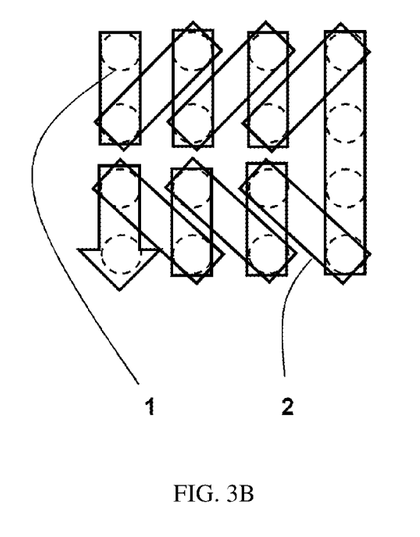

For this purpose, FIGS. 1 to 3 show different variants of a line progression of a target beam juxtaposed from a plurality of lines.

Specifically, FIG. 1 shows spiral juxtaposed line progressions of the target beam for the pre-display of a 3×3 and a 4×4 spot pattern, FIG. 2 shows meandering juxtaposed line progressions of the target beam for the pre-display of a 4×4 spot pattern and FIG. 3 shows zigzag juxtaposed line progressions of the target beam for the pre-display of a 4×4 spot pattern.

In all FIGS., the individual spots 1 are shown as dashed circles and the lines of the target beam 2 are shown as an arrow, wherein the target beam 2 overlies all spots 1 of the spot pattern in each case.

The line progressions of the target beam, shown in the FIGS., for the pre-display of spot patterns are only exemplary here, since there are a multiplicity of possibilities, particularly in the case of larger spot patterns, for juxtaposing the line progressions.

In principle, however, the one or more lines of the target beam can be juxtaposed in any desired way.

Figure 4:
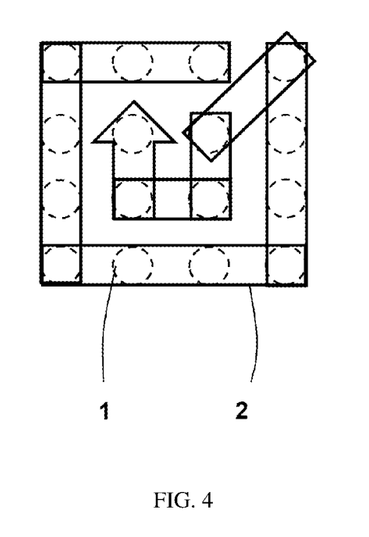
FIG. 4 depicts an arbitrarily juxtaposed line progression of the target beam for the pre-display of a 4×4 spot pattern

In this respect, FIG. 4 shows an arbitrarily juxtaposed line progression of the target beam for the pre-display of a 4×4 spot pattern. Here, too, the individual spots 1 are shown as dashed circles and the lines of the target beam 2 are shown as an arrow, which overlies all spots 1 of the spot pattern.

Here, the one or more lines of the target beam generated by the laser system and the scanning system can either be rectilinear or describe a circular arc or another shape.

For this purpose, the laser system and the scanning system are designed to depict the juxtaposed line progression made of lines which are rectilinear, circular arcs or describe another shape, wherein the travel speed of the scanning system within a line of the line progression reaches a value >50 mm/s.

According to example embodiments of the invention, the scanning system is to be dimensioned such that the total time for pre-displaying an entire spot pattern once (regardless of the number of spots) is in a range from 0.1 ms to 100 ms. In order to allow the practitioner enough time to set up his spot pattern when the pre-display is continuously available, the pre-display of an entire spot pattern is repeated continuously, in particular without breaks.

If need be, it can be expedient for a wide variety of reasons to generate one or more lines that overlie only a portion of the spots of the spot pattern of a planned laser treatment.

For this purpose, preferably only the spots of the spot pattern of a planned laser treatment that form the outer frame of the spot pattern are overlaid.

Figure 5:
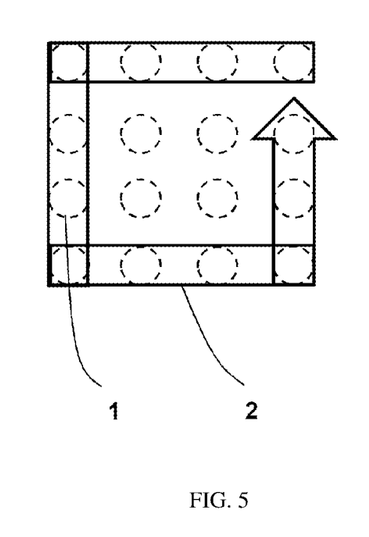
FIG. 5 depicts a juxtaposed line progression of the target beam for the pre-display of a 4×4 spot pattern in which not all the spots of the spot pattern are overlaid.
Figure 6:
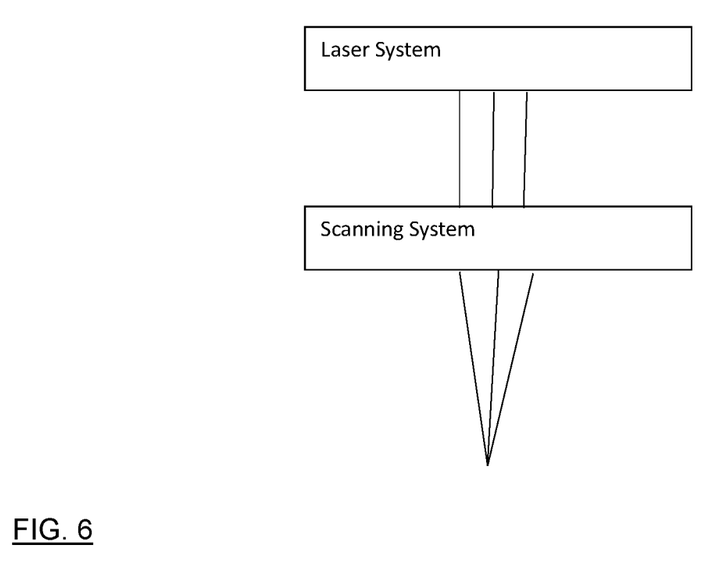
FIG. 6 depicts a the "laser system" and "scanning system" according to an example embodiment of the invention.

In this respect, FIG. 5 shows a juxtaposed line progression of the target beam for the pre-display of a 4×4 spot pattern in which only the outer spots of the spot pattern are overlaid. The individual spots 1 are again shown as dashed circles and the lines of the target beam 2 are shown as an arrow.

While the individual laser spots within the juxtaposed line progression are not shown in accordance with this first example embodiment, in the following embodiment variants the individual laser spots within the juxtaposed line progression are additionally shown.

In accordance with a first example embodiment variant, the scanning system is formed to additionally show the individual laser spots within the juxtaposed line progression, by virtue of the scan movement being decreased or briefly stopped at their positions.

Here, while maintaining the line-shaped pre-display, there is an intervention in the temporal course of the scan by the positions of the individual laser spots being taken into account and at these points the target beam being shown for longer at these positions by application of a short rest position of the scanning system. The continuous line progression is thus visually preserved and the positions of the individual laser spots are additionally emphasized more clearly.

According to an example embodiment of the invention, the holding time of the target beam at an individual position of a laser spot is between 1 and 20 ms.

In accordance with a second example embodiment, the laser system is formed to additionally represent the individual laser spots within the juxtaposed line progression. According to example embodiments of the invention, this can take place by use of various variants.

In a first example variant, this is done by virtue of the intensity of the target beam being briefly increased significantly at their positions.

According to the invention, the intensity is increased in the range of a factor of 1.2 to a factor of 10 and in particular, for example, by a factor of 1.5.

Here, while maintaining the line-shaped display, there is an intervention in the intensity of the target beam brightness by taking into account the positions of the individual laser spots and visibly increasing the intensity of the target beam brightness at these points. Here, too, the continuous line progression is visually preserved and the positions of the individual laser spots are additionally emphasized more clearly.

In a second example variant, this is done by virtue of the wavelength of the target beam being significantly changed at said positions. In particular, a second target beam with a different wavelength is provided, wherein the two target beams are coaxial with one another.

While maintaining the line-shaped display, here there is an intervention in the wavelength of the target beam and the wavelength of the target beam is significantly changed at the positions of the individual laser spots.

This is done either by switching on the second target beam or by briefly changing from the first to the second target beam.

Again, the continuous line progression is visually preserved and the positions of the individual laser spots are additionally emphasized more clearly.

According to the invention, the wavelength is changed by, for example, at least 10 nm.

With a wavelength of the first target beam of 635 nm (light red), it is sufficient, for example, if the second target beam has a wavelength of 670 nm (dark red).

In order to emphasize the positions of the individual laser spots even more clearly, however, it is also possible to use a second target beam with a wavelength of 532 nm (green).

The two wavelengths mentioned here for the second target beam are only examples and can be chosen freely.

According to a third example embodiment, the laser system and the scanning system for generating a target beam are formed to continuously display the juxtaposed line progression of the spot pattern of a planned laser treatment.

This presents the operator with an almost "stationary image" of the spot pattern until the operator triggers the laser treatment.

According to a fourth example embodiment, the laser system and the scanning system for generating a target beam are formed to generate one or more additional lines which overlie all the spots of a subsequent spot pattern of the planned laser treatment, and to represent said lines as a juxtaposed line progression.

As a result, after the laser treatment of a spot pattern has been carried out, the pre-display according to the invention of a subsequent spot pattern of the planned laser treatment can take place, wherein this for example takes place automatically and in a manner accurately matched to the therapeutic spot pattern.

In the example method for the pre-display of a spot pattern to be applied for a laser treatment of the eye, a target beam is generated by a laser system and a scanning system, said beam being in the form of one or more lines which overlie all the spots of the spot pattern of a planned laser treatment.

According to example embodiments of the invention, the one or more line(s) of the target beam is/are depicted as a juxtaposed line progression which is formed as rectilinear, curved or otherwise.

Regardless of how the one or more lines of the target beam are juxtaposed to make a line progression, individual or even all laser spots are arranged at the turning points, i.e. at the points with a change of direction.

When juxtaposing the one or more lines of the target beam, it is advantageous, for example, to take into account the movement of the scanning system. Spiral, meandering or zigzag juxtapositions, for example, are therefore preferable. In principle, however, the one or more lines of the target beam can be juxtaposed in any desired way.

The juxtaposition of the one or more lines of the target beam to make a line progression is achieved by the scanning system first accelerating the target beam from a beginning of the line to the end of the line and then decelerating the target beam, in order to accelerate the next line progression at the point of direction change and then to decelerate it again until all lines are connected to form a line progression and the entire spot pattern of a planned laser treatment was displayed.

According to the invention, the total time for pre-displaying a complete spot pattern once (regardless of the number of spots) is in a range from 0.1 ms-100 ms. In order to allow the practitioner enough time to set up his spot pattern when the pre-display is continuously available, the pre-display of an entire spot pattern is repeated continuously, in particular without breaks.

If need be, it can be expedient for a wide variety of reasons to generate one or more lines that overlie only a portion of the spots of the spot pattern of a planned laser treatment. For this purpose, for example only the spots of the spot pattern of a planned laser treatment that form the outer frame of the spot pattern are overlaid.

While the individual laser spots within the juxtaposed line progression are not shown in accordance with this embodiment, in the following example embodiment variants the individual laser spots within the juxtaposed line progression are additionally shown.

In accordance with a first example embodiment variant of the method, the individual laser spots within the juxtaposed line progression are additionally shown, by virtue of the scan movement being decreased or briefly stopped at their positions.

Here, while maintaining the line-shaped pre-display, there is an intervention in the temporal course of the scan by the positions of the individual laser spots being taken into account and at these points the target beam being shown for longer at these positions by a short rest position of the scanning system. The continuous line progression is thus visually preserved and the positions of the individual laser spots are additionally emphasized more clearly.

According to a further example embodiment of the invention, the holding time of the target beam at an individual position of a laser spot is between 1 and 20 ms.

In accordance with a second example embodiment of the method, the individual laser spots within the juxtaposed line progression are additionally represented, by virtue of the intensity of the target beam being briefly increased significantly at their positions.

Here, while maintaining the line-shaped display, there is an intervention in the intensity of the target beam brightness by taking into account the positions of the individual laser spots and visibly increasing the intensity of the target beam brightness at these points. Here, too, the continuous line progression is visually preserved and the positions of the individual laser spots are additionally emphasized more clearly.

According to another example embodiment of the invention, the intensity is increased by a factor of 1.5 or greater.

In accordance with a third example embodiment of the method, the individual laser spots within the juxtaposed line progression are additionally represented, by virtue of the wavelength of the target beam being significantly changed at their positions. In particular for example, a second target beam with a different wavelength is provided, wherein the two target beams are coaxial with one another.

While maintaining the line-shaped display, here there is an intervention in the wavelength of the target beam and the wavelength of the target beam is significantly changed at the positions of the individual laser spots.

This is done either by switching on the second target beam or by briefly changing from the first to the second target beam.

Again, the continuous line progression is visually preserved and the positions of the individual laser spots are additionally emphasized more clearly.

According to the invention, the wavelength is changed by, for example, at least 10 nm.

With a wavelength of the first target beam of 635 nm (light red), it is sufficient, for example, if the second target beam has a wavelength of 670 nm (dark red).

In order to emphasize the positions of the individual laser spots even more clearly, however, it is also possible to use a second target beam with a wavelength of 532 nm (green).

The two wavelengths mentioned here for the second target beam are only examples and can be chosen freely.

In accordance with a fourth example embodiment of the method, the juxtaposed line progression of the spot pattern of a planned laser treatment is continuously displayed.

This presents the operator with an almost "stationary image" of the spot pattern until the operator triggers the laser treatment.

According to a further embodiment of the method, the laser system and the scanning system for generating a target beam are formed to generate one or more additional lines which overlie all the spots of a subsequent spot pattern of the planned laser treatment, and to represent said lines as a juxtaposed line progression.

As a result, after the laser treatment of a spot pattern has been carried out, the pre-display according to the invention of a subsequent spot pattern of the planned laser treatment can take place, wherein this for example takes place automatically and in a manner accurately matched to the therapeutic spot pattern.

With the example embodiments of the invention, a solution is made available with which the spot patterns to be applied are displayed to the operator in advance with the aid of a target beam (without therapeutic effect).

With example embodiments of the invention for the pre-display of a spot pattern to be applied for laser treatment of the eye, the disadvantages of the solutions in the prior art are eliminated and the spot patterns can be displayed reliably and quickly. In particular, the solution allows a "stationary image" of the spot patterns to be displayed as "stationary" as possible even when using relatively slow scanning systems.

According to example embodiments of the invention, a target beam is generated by a laser system and a scanning system, said beam being in the form of one or more line(s) which overlie all the spots of the spot pattern of a planned laser treatment. Preferably, the one or more line(s) of the target beam can be formed as rectilinear, curved or otherwise, wherein the travel speed within a line of the line progression reaches a value >50 mm/s.

A particular advantage can be seen in the fact that a juxtaposed line progression is generated from the one or more lines of the target beam and is continuously displayed, as a result of which the operator is presented with an almost "stationary image" of the spot pattern.

According to an example embodiment, it is provided that the individual laser spots are additionally shown within the juxtaposed line progression. According to the invention, for this purpose, at the positions of the individual laser spots, the scan movement is decreased or briefly stopped, the intensity of the target beam is briefly increased significantly, or the wavelength of the target beam is changed significantly.

Example embodiments of the invention are intended for laser treatment of the eye, in which a spot pattern to be applied is pre-displayed by a target beam before the actual laser treatment on the eye is carried out. Here, the solution is suitable for the laser treatment of the retina, the trabecular meshwork or else other regions.

It is also irrelevant whether the laser treatment is a minimally invasive method for thermal stimulation, selective retina therapy or selective laser trabeculoplasty or laser coagulation for denaturing tissue.

The invention claimed is:

1. A device for pre-display of a spot pattern to be applied for a laser treatment of an eye, comprising:
   a laser system and a scanning system that together generate a target beam;
   wherein the spot pattern is predefined and includes a pattern of predefined spots at which laser energy is to be applied to accomplish the laser treatment of the eye;
   wherein the laser system and the scanning system that together generate the target beam are formed to generate one or more continuous lines of light which simultaneously appear to overlie all spots of the spot pattern of a planned laser treatment thus pre-displaying the spot pattern;
   wherein the laser system and the scanning system are configured to generate a treatment beam to apply treatment laser energy to the predefined spots.

2. The device as claimed in claim 1, wherein the laser system and the scanning system are formed to represent the one or more lines of the target beam as a juxtaposed line progression that is rectilinear or that describes a circular arc, wherein the total time for displaying the spot pattern once is in the range of 0.1 ms-100 ms.

3. The device as claimed in claim 1, wherein the laser system and the scanning system are formed to represent the one or more lines of the target beam as a juxtaposed line progression that is rectilinear or describes a circular arc, wherein the travel speed within a line of the line progression reaches a value >50 mm/s.

4. The device as claimed in claim 1, wherein the scanning system is formed additionally to represent the individual laser spots within a juxtaposed line progression, by virtue of the scan movement being decreased or briefly stopped at their positions, wherein a holding time of the target beam at the individual position of a laser spot is between 1 and 20 ms.

5. The device as claimed in claim 1, wherein the laser system is formed additionally to represent the individual laser spots within a juxtaposed line progression, by virtue of the intensity of the target beam being briefly increased significantly at their positions, wherein the intensity is increased in the range of a factor of 1.2 to a factor of 10 or by a factor of 1.5.

6. The device as claimed in claim 5, wherein the laser system is formed additionally to represent the individual laser spots within the juxtaposed line progression, by virtue of the intensity of the target beam being briefly increased significantly at their positions, wherein the intensity is increased by a factor of 1.5.

7. The device as claimed in claim 1, wherein the laser system is formed additionally to represent the individual laser spots within a juxtaposed line progression, by virtue of the wavelength of the target beam being significantly changed at their positions, wherein the wavelength is changed by at least 10 nm.

8. The device as claimed in claim 1, wherein the laser system and the scanning system that together generate a target beam are formed to continuously display a juxtaposed line progression of the spot pattern of a planned laser treatment.

9. The device as claimed in claim 1, wherein the laser system and the scanning system that together generate a target beam are formed to generate one or more additional lines which overlie all the spots of a subsequent spot pattern of the planned laser treatment, and to represent said additional lines as a juxtaposed line progression.

10. A method for pre-display of a spot pattern to be applied for a laser treatment of an eye, comprising:
defining spots of the spot pattern for a planned laser treatment;
presenting a target beam which is generated by a laser system and a scanning system; and
generating the target beam in the form of one or more continuous lines of light which simultaneously appear to overlie all the spots of the spot pattern of the planned laser treatment thus pre-displaying the spot pattern.

11. The method as claimed in claim 10, further comprising representing one or more lines of the target beam as a juxtaposed line progression, which is formed as rectilinear, or curved, wherein the total time for displaying a spot pattern once is in the range of 0.1 ms-100 ms.

12. The method as claimed in claim 10, further comprising representing the one or more lines of the target beam is as a juxtaposed line progression, which is formed as rectilinear, or curved, wherein the travel speed within a line of the line progression reaches a value >50 mm/s.

13. The method as claimed in claim 10, further comprising additionally representing the individual laser spots within the juxtaposed line progression, by virtue of the scan movement being decreased or briefly stopped at their positions, wherein a holding time of the target beam at an individual position of a laser spot is between 1 and 20 ms.

14. The method as claimed in claim 10, further comprising additionally representing the individual laser spots within a juxtaposed line progression, by virtue of an intensity of the target beam being briefly increased significantly at their positions, wherein the intensity is increased in the range of a factor of 1.2 to a factor of 10 or by a factor of 1.5.

15. The method as claimed in claim 14, further comprising additionally representing the individual laser spots within a juxtaposed line progression, by virtue of an intensity of the target beam being briefly increased significantly at their positions, wherein the intensity is increased by a factor of 1.5.

16. The method as claimed in claim 10, further comprising additionally representing the individual laser spots within a juxtaposed line progression, by virtue of a wavelength of the target beam being significantly changed at their positions, wherein the wavelength is changed by at least 10 nm.

17. The method as claimed in claim 10, further comprising continuously displaying a juxtaposed line progression of the spot pattern of a planned laser treatment.

18. The method as claimed in claim 10, further comprising generating one or more additional lines which overlie all the spots of a subsequent spot pattern of the planned laser treatment and representing the one or more additional lines as a juxtaposed line progression.

* * * * *

UNITED STATES PATENT AND TRADEMARK OFFICE
CERTIFICATE OF CORRECTION

| | |
|---|---|
| PATENT NO. | : 11,951,042 B2 |
| APPLICATION NO. | : 17/045665 |
| DATED | : April 9, 2024 |
| INVENTOR(S) | : Dick et al. |

It is certified that error appears in the above-identified patent and that said Letters Patent is hereby corrected as shown below:

In the Specification

Column 2, Line 28, delete "2014" and insert --2014.--

Column 3, Line 26, delete "pattern" and insert --pattern,--

Column 3, Line 30, delete "a the" and insert --a--

Column 3, Line 38, delete "to gather" and insert --together--

In the Claims

Column 10, Line 7, delete "beam is" and insert --beam--

Signed and Sealed this
Twenty-third Day of July, 2024

*Katherine Kelly Vidal*

Katherine Kelly Vidal
*Director of the United States Patent and Trademark Office*